United States Patent
Igel et al.

(10) Patent No.: US 6,471,838 B1
(45) Date of Patent: Oct. 29, 2002

(54) MEASURING DEVICE AND PROCESS FOR ITS MANUFACTURE

(75) Inventors: Günter Igel, Teningen; Hans-Jürgen Gahle, Emmendingen; Mirko Lehmann, Freiburg, all of (DE)

(73) Assignee: Micronas GmbH, Feiburg (DE)

( * ) Notice: Subject to any disclaimer, the term of this patent is extended or adjusted under 35 U.S.C. 154(b) by 0 days.

(21) Appl. No.: 09/506,646

(22) Filed: Feb. 18, 2000

(30) Foreign Application Priority Data

Feb. 19, 1999 (DE) .......................................... 199 07 164

(51) Int. Cl.⁷ ..................... G01N 27/327; G01N 27/333
(52) U.S. Cl. ................... 204/403.01; 204/416
(58) Field of Search ................ 204/400, 403, 204/409, 416, 403.01; 422/58, 59, 60, 82.01, 82.02, 82.03, 82.05; 436/63, 150

(56) References Cited

U.S. PATENT DOCUMENTS

| | | | |
|---|---|---|---|
| 5,035,791 A | 7/1991 | Battilotti et al. | 204/415 |
| 5,240,586 A | 8/1993 | Moore et al. | 204/418 |
| 5,278,012 A | 1/1994 | Yamanaka et al. | 430/30 |
| 5,430,347 A | * 7/1995 | Kane et al. | 313/309 |
| 5,851,489 A | 12/1998 | Wolf et al. | 422/82.02 |

FOREIGN PATENT DOCUMENTS

| | | |
|---|---|---|
| DE | 195 29 371 C2 | 1/1998 |
| DE | 44 17 078 C2 | 4/1998 |
| DE | 197 12 309 A1 | 5/1998 |
| EP | 0 299 778 A2 | 1/1989 |
| EP | 0 585 933 A2 | 3/1994 |
| WO | WO 95/01559 | 1/1995 |

OTHER PUBLICATIONS

Baumann, W.H., et al., "Microelectronic Sensor System for Microphysiological Application on Living Cells," *Sensors and Actuators B*, 55: 77–89 (1999).

* cited by examiner

*Primary Examiner*—T. Tung
*Assistant Examiner*—Alex Noguerola
(74) *Attorney, Agent, or Firm*—Akin, Gump, Strauss, Hauer & Feld, L.L.P.

(57) ABSTRACT

A measuring device (1), for examining a medium (2) that is liquid or free-flowing, has at least two electrically and/or optically conducting layers or layer areas (5a, 5b, 5c, 6a, 6b, 7a, 7b) located on a substrate layer (3), wherein these layers or layer areas are electrically and/or optically insulated from each other. At least one of these layers or layer areas (5a, 5b, 5c, 6a, 6b, 7a, 7b) is part of a layer stack (4), which has several layers arranged on top of each other on the substrate layer (3). The layer stack has, on its side facing away from the substrate layer (3), a recess that adjoins the electrically and/or optically conducting layers or layer areas (5a, 5b, 6a, 6b, 7a, 7b). At least one electrically and/or optically conducting layer or layer area (5a, 5b, 6a, 6b, 7a, 7b) located in the layer stack (4) is spaced at a distance from the bottom (11) of the recess (10).

17 Claims, 2 Drawing Sheets

MEASURING DEVICE AND PROCESS FOR ITS MANUFACTURE

BACKGROUND OF THE INVENTION

The invention relates to a measuring device for examining a medium, especially one that is liquid or free-flowing, and a process for manufacturing a measuring device of this type.

From PCT publication WO 95/31716 a measuring device is already known which has an electrically conducting layer located on a substrate layer and having two layer areas each arranged in the plane of the layer and electrically insulated from each other. The two layer areas form electrodes which have approximately the shape of a comb. The layer areas mesh into each other with their comb structures. This previously known measurement device has proven valuable in practice, especially for the physiological examination of biological cells which are arranged in a nutrient medium and adhere during measurement to the surface of the substrate layer and the planar conducting layer areas located on it. With this previously known measurement device, on the one hand, conductivity measurements can be performed on a cell membrane area of the cells located in the deposit area of the cells, and on the other hand, the measurement device also makes possible a capacitive uncoupling of electric signals from the cell membrane.

A disadvantage of this previously known measurement device, however, still exists in that it only allows an examination of the cells on the conductive layer areas and the underside of the cells which is facing the substrate layer. It has been revealed, however, that biological cells can have different electric and/or optical properties in various areas of their cell membrane which, for example, can be brought forth by a locally varying diffusion of ions or proteins located in the cell liquid of the cells.

SUMMARY OF THE INVENTION

Therefore, an object of the invention is to create a measurement device, of the type described above, which allows for further examination of the medium. In addition, an object of the invention is to provide a process for manufacturing such a measuring device.

This object is achieved in that the measuring device has at least two electrically and/or optically conducting layers or layer areas made of a solid material and located on a substrate layer, wherein these layers or layer areas are electrically and/or optically insulated from each other, in that at least one of these layers or layer areas is arranged in a layer stack, which has several layers arranged on top of each other on the substrate layer, in that the layer stack has, on its side facing away from the substrate layer, a recess that adjoins the electrically and/or optically conducting layers or layer areas; and in that at least one layer located in the layer stack, which is electrically and/or optically conducting, or the at least one layer area located in the layer stack, which is electrically and/or optically conducting, is spaced at a distance from the bottom of the recess.

The measuring device thus has a layer stack with a recess, adjoined by at least one electrically and/or optically conducting layer or one layer area of the layer stack, which is set off at a distance from the bottom of the recess by at least one additional layer. Thus, on the limiting wall of the recess, an electrically conducting and/or optically transparent wall area is produced, which is arranged at a distance from the bottom of the recess. In this way, it is possible to emit electrical and/or optical signals into the medium located in the recess, or to receive them from the medium, at a position spaced from the bottom of the recess. In a measuring device which is electrically conducting at the layer or layer area adjacent to the recess and spaced from the bottom of the recess, conductivity measurements or capacitive measurements, for example, can be carried out, for example in a direction transverse to the extension plane of the substrate layer or in a direction running parallel to it, on the medium located in the recess and/or particles contained in it, for example biological cells which have settled on the bottom of the recess.

In a measuring device in which the layer or layer area spaced from the bottom of the recess and adjacent to the recess is optically transparent, it is even possible to measure the optical transmission or emission in the medium in a direction running transversely to the extension plane of the substrate layer or in a direction parallel to it. A transmission measurement can occur, for example, such that through one of the optically transparent layers or layer areas, an optical radiation is coupled into the recess and transmitted through the medium to the other optically transparent layer, and via this layer it is uncoupled again from the recess. The measurement device thus allows a three-dimensional investigation of a medium located in the recess.

In an advantageous way, with the electrically and/or optically conducting layer, which is spaced from the bottom of the recess in the limiting wall of the recess and oriented with its active surface transverse to the coating plane of the substrate layer, a compactly designed measurement device is produced, which requires only a comparatively small area on the substrate layer. In a measuring device constructed as a semiconductor chip, expensive chip area can thus be saved.

In one advantageous embodiment of the invention, at least one layer of the layer stack has at least two electrically and/or optically conducting layer areas arranged next to each other in the coating plane of this layer, each being adjacent to the recess and insulated from each other electrically and/or optically. The medium located in the recess can then be examined optically and/or electrically at a distance from the bottom of the recess in the coating plane of this layer. It is even possible herein that the layer have more than two layer areas, each adjacent on the sides of the recess and electrically and/or optically conducting, so that the medium located in the recess can then be examined in different directions in the coating plane of this layer, depending on between which of these layer areas in the recess, an optical and/or electrical measuring path is formed.

It is especially advantageous if, on each side of an optically conducting layer or layer area, a metallic layer or layer area is arranged transverse to the coating plane as an optical reflection layer. Radiation losses in the layers adjacent to the optically conducting layer are thereby reduced. The metallic. layers adjacent to the optical layer can optionally be adjacent to the recess, so that these layers also allow coupling and/or uncoupling of electric signals into the optically conducting layer outside of a guide for the optical radiation.

In one especially advantageous embodiment of the invention, on the limiting wall of the recess, at least one electric and/or optically conducting layer area forms a projection relative to at least one layer area adjacent to it, and the layer area having the projection and the layer area adjacent to it are preferably arranged in different coating planes of the layer stack. In an electric layer a small ohmic contact resistance then occurs between the layer and the medium located in the recess, while in an optically conducting layer the projection allows a small optical radiation resistance between the layer and the medium.

In one advantageous embodiment of the invention, the limiting wall of the recess has at least one coupling location, which is located on an optically conducting layer and/or on an optically conducting layer area, for the targeted emission of optical radiation into the recess. In the limiting wall, lying opposite the coupling position in the emission direction of the radiation, at least one uncoupling position is arranged on an optically transparent layer or layer area. The coupling position and/or the uncoupling position is (are) arranged on a projection which projects into the recess beyond the layers on both sides adjacent to it and can be extended against the restoring force of its material from a rest position transverse to the coating plane of the layer having the projection. The measuring device then allows the measurement of dynamic pressure changes in the medium to be examined, which is located in the recess.

A dynamic pressure change in the medium, or a pressure wave that propagates transversely to the extension direction of the projection in the medium, causes an excursion of the projection having the coupling or uncoupling position from its resting position, such that the transmission path is, changed at the uncoupling position by optical radiation radiated into the medium at the coupling position. A dynamic pressure change in the medium thus leads to a change of the optical signal uncoupled from the medium at the uncoupling position, which can be detected by a corresponding optical sensor. This can be integrated in the layer stack and/or optically connected to the uncoupling-side, optically transparent layer or layer area.

An expedient embodiment of the invention has at least one sensor arranged in the bottom of the recess for examining the medium located in the recess. The sensor can be, for example, a field effect transistor for detecting ions contained in the medium, a sensor for measuring a gas content and/or an optical sensor. The medium located in the recess can then be even further examined. Thus, for example, using the sensor, measurements can be made on a cell in a nutrient medium, which is located in the recess and contains the biological cell that settles on the bottom of the recess.

It is advantageous if an ion-selective membrane is arranged in the recess that preferably grasps behind a projection of the limiting wall of the recess. The layers or layer areas located on the wall area covered by the membrane and/or a sensor optionally located in the bottom of the recess then makes possible a detection of certain ions contained in the medium and to which the membrane is permeable, while other ions or particles are kept away from these layers and/or layer areas and/or the sensor. With a membrane that grasps behind a projection of the limiting wall of the recess, an especially good adhesive force of the membrane results on the layer stack.

In another advantageous embodiment of the invention, the layer stack has several recesses, preferably having different dimensions and arranged in an array-shape, which each adjoin at least two electrically and/or optically conducting layers or layer areas. At least one of the layers or layer areas adjoining the respective recess is arranged at a distance from the bottom of the recess. The openings of the differently dimensioned recesses then form a mechanical filter for particles contained in the medium to be examined, so that with the measuring devices formed by the respective individual recesses and layers or layer areas adjoining them, particles having different sizes can be examined. In addition, the recesses of the individual measurement devices can have different volumes, so that depending on the quantity of the liquid or flee-flowing medium to be examined, a recess can be chosen with a volume that is fitted to the quantity of the medium.

In regard to the process for manufacturing a measuring device of the type mentioned at the outset, the above object is achieved by mounting layers on a substrate layer to form a layer stack having at least two electrically and/or optically conducting layers, between which at least one electrically and/or optically insulating intermediate layer is arranged. On the side of the layer stack facing away from the substrate layer, a recess is made in the layer stack, which penetrates the electrically and/or optically conducting layers and/or adjoins them on the side.

In addition to the already mentioned advantages of the measuring device, the process has the additional advantage that it can be integrated well into the manufacturing process for producing a semiconductor chip, in particular a CMOS-chip. The layers mounted on the substrate layer during the manufacture of the layer stack can additionally be used for the manufacture of other structures to be integrated into the semiconductor chip, for example strip conductors, transistors, and/or sensors, in which these layers are masked in a customary manner, for example using a photo-lithographic process. It is especially advantageous in the process that the recess is made in the layer stack only after the production of all layers necessary for the layer stack, i.e., the photo-resist layers necessary for the photolithographic manufacture of the additional structures of the semiconductor chip are each applied on the individually interconnected mounted layers of the layer stack before the recess is made in the layer stack. In this way, the recess cannot prevent the photo-resist, applied for example by a rotational molding process, from spreading out on the surface of the separate layers. Also, formation of tears, which can occur when a layer is applied onto an edge or a shoulder, is prevented by the subsequent creation of the recess in the layer stack.

The above object of the invention can also be achieved in terms of the process, wherein a substrate layer is provided with a layer stack by mounting at least one electrically and/or optically insulating first layer and at least one electrically and/or optically conducting second layer, such that on the side of the layer stack facing away from the substrate layer a recess adjoining the electrically and/or optically conducting second layer and/or penetrating through it is created in the layer stack, and such that on the bottom of the recess at least one electrically and/or optically conducting third layer is arranged spaced from the second layer.

This process also allows the manufacture of a three-dimensional measuring device having a layer that is spaced from the bottom of the recess and that is electrically and/or optically conducting. In addition, however, the bottom of the recess is itself also electrically and/or optically conducting and can also be used to examine a medium located in the recess. The process can be integrated well into the manufacturing process for a semiconductor chip.

Finally, the above object can be achieved in terms of the process, wherein a layer stack is provided on a substrate layer by creating at least one electrically and/or optically insulating layer and at least one electrically and/or optically conducting layer; the electrically and/or optically conducting layer is subdivided into at least two electrically and/or optically conducting layer areas, which are electrically and/or optically insulated from each other; and a recess that penetrates and/or adjoins the electrically and/or optically conducting layer areas is made in the layer stack on the side of the layer stack facing away from the substrate layer, so that the bottom of the recess is spaced from the electrically and/or optically conducting layer areas. This process has the advantage that the measuring device manufactured thereby allows an examination of the medium located in the recess in the plane of the electrically and/or optically conducting layer that contains the layer areas.

In an especially advantageous embodiment of the process, an indentation relative to an adjacent electrically and/or optically conducting layer or layer area is formed by removing layer material on the limiting wall of the recess in the region of an electrically and/or optically insulating layer or layer area. In an electrically conducting layer or layer area a small transition resistance results between the layer or the layer area and the medium to be examined which is located in the recess. Electric signals can be better coupled and/or uncoupled into or out of the medium in this way. Correspondingly, the indentation in an optically conducting layer or layer area allows a small optical transition resistance between the layer or the layer area and the medium.

In an especially advantageous embodiment of the process, the layer stack is brought into contact with an etchant in order to create the recess, and the layer materials of the individual layers or layer areas are selected in such a way, in order to form the indentation in the limiting wall of the recess, that they have different etching rates with regard to the etchant. The limiting wall of the recess can be provided with indentations or a layered profiling in a simple way.

It is advantageous if the substrate is provided with a layer stack having, transverse to the coating plane of its layers, a metallic layer as an optical reflection layer on both sides of an optically conducting layer or layer area. The metallic layers function then, on the one hand, as an optical reflection layer and can, on the other hand, also be used to couple electric signals into and/or uncouple electric signals from the medium.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiment(s) which are presently preferred. It should be understood, however, that the invention is not limited to the precise arrangements and instrumentalities shown. In the drawings.

DETAILED DESCRIPTION OF THE INVENTION

Figure 1:
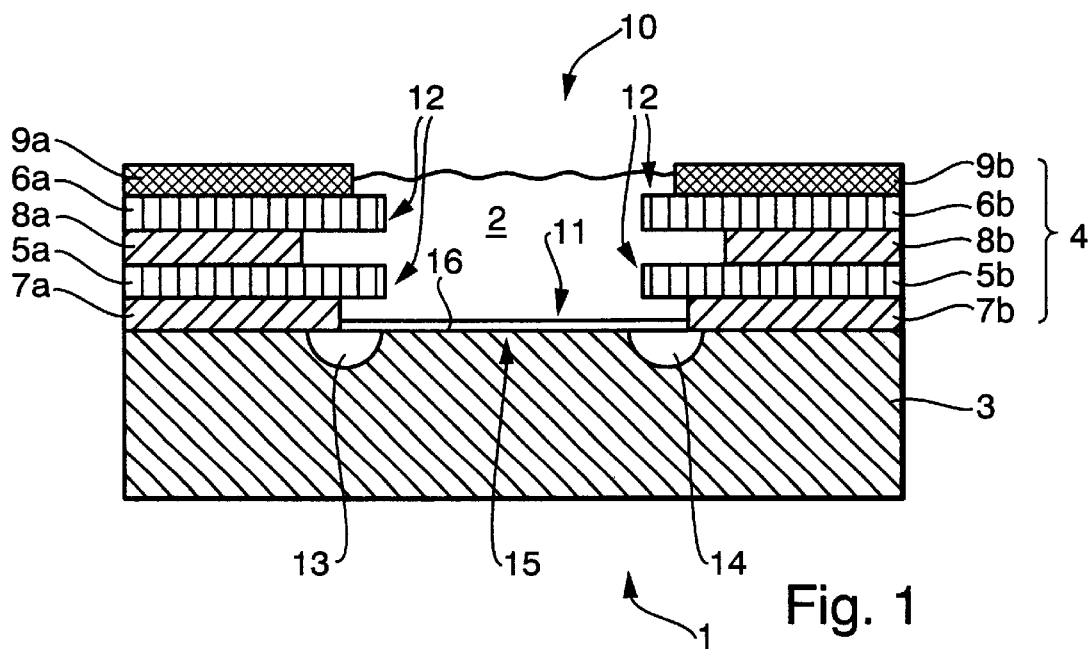
FIG. 1 is a cross-section through a measuring device, which has a layer stack with a recess containing a liquid medium, the limiting wall of which has a profiling with layered projections and indentations.

A measuring device (FIG. 1) indicated as a whole by 1, for examining a liquid or free-flowing medium 2, has a layer stack 4 arranged on a substrate layer 3, which has several electrically conducting layer areas 5a, 6a. An electrically insulating layer area 8a, 8b, which consists of an optically conducting material, is arranged between each of the adjacent layer areas 5a, 6a or 5b, 6b, running transverse to the layer planes of the layer stack 4. An additional optically conducting and electrically insulating layer area 7a, 7b is arranged between the substrate layer 3 and the layer areas 5a, 5b. On the upper side of the layer stack 4, facing away from the substrate layer 3, the layer stack has a passivation layer 9a, 9b. In the embodiment according to FIG. 2, the passivation layer is indicated by 9.

The layer stack 4 has a recess 10, bordered by the layer areas 5a, 5b, 6a, 6b, 7a, 7b, 8a, 8b, 9a, 9b of the layer stack 4, on its upper side facing away from the substrate layer 3. The recess 10 is constructed as a conducting-state channel, which penetrates the layer stack 4 in the direction of its coating planes approximately at a right angle to the symbol plane in FIG. 1.

The medium 2 located in the recess 10 can be electrically examined using the electrically conducting layer areas 5a, 5b, 6a, 6b and can be optically examined using the optically conducting layer areas 7a, 7b, 8a, 8b. Thus, for example, the conductivity of the medium 2 can be measured in different coating planes of the layer stack 4 by applying an electrical voltage between the layer areas 5a, 5b and/or the layer areas 6a, 6b and measuring the electric current between the electrodes formed by these layer areas 5a, 5b, 6a, 6b. The conductivity of the medium 2 can, however, also be determined in a direction running perpendicular to the coating planes of the layer stack 4, by an electric voltage being applied between the layer areas 5a, 6a and/or 5b, 6b and measuring the electric current between these layer areas 5a, 6a or 5b, 6b. In a corresponding manner, the conductivity of the medium 2 can also, however, be determined in a direction running at an oblique angle to the coating planes of the layer stack 4, if an electric voltage is applied between both sides of the recess 10 and layer areas 5a, 6b or 5b, 6a arranged in different coating planes, and the current between these layer areas 5a, 6b or 5b, 6a is measured. In a corresponding manner, the dielectric constant of the medium can be measured in different directions using the electrically conducting layer areas 5a, 5b, 6a, 6b.

Using the optically conducting layer areas 7a, 7b, 8a, 8b, the medium 2 can also be optically examined. Thus, for example, the optical transmission of the medium 2 can be measured in different directions, by coupling optical radiation (light) through one of the layer areas 7a, 7b, 8a, 8b at a time into the medium 2, and by uncoupling the radiation portion transmitted through the medium 2 out of the medium 2 again, using one or more of the other optically conductive layer areas 7a, 7b, 8a, 8b. Of course, the layer areas 5a, 5b, 6a, 6b, 7a, 7b, 8a, 8b can also function for uncoupling electrical and/or optical signals emerging from the medium 2 itself. Thus, for example, using the optically conducting layer areas 7a, 7b, 8a, 8b, fluorescence measurements can be carried out on the medium 2, when it is excited to fluorescence, for example by optical radiation through the opening located on the upper side of the recess 10. In addition, using the electrically conducting layer areas 5a, 5b, 6a, 6b, electric signals can be picked up on electrically active particles located in the medium 2, for example nerve cells contained in a nutrient medium.

In the embodiment according to FIG. 1, the layer areas 5a, 5b, 6a, 6b comprise a metallic material, which functions as a reflection layer for optical signals transported into the layer areas 7a, 7b, 8a, 8b. The layer areas 7a, 7b, 8a, 8b thereby allow a low-loss optical wave guide.

Figure 2:
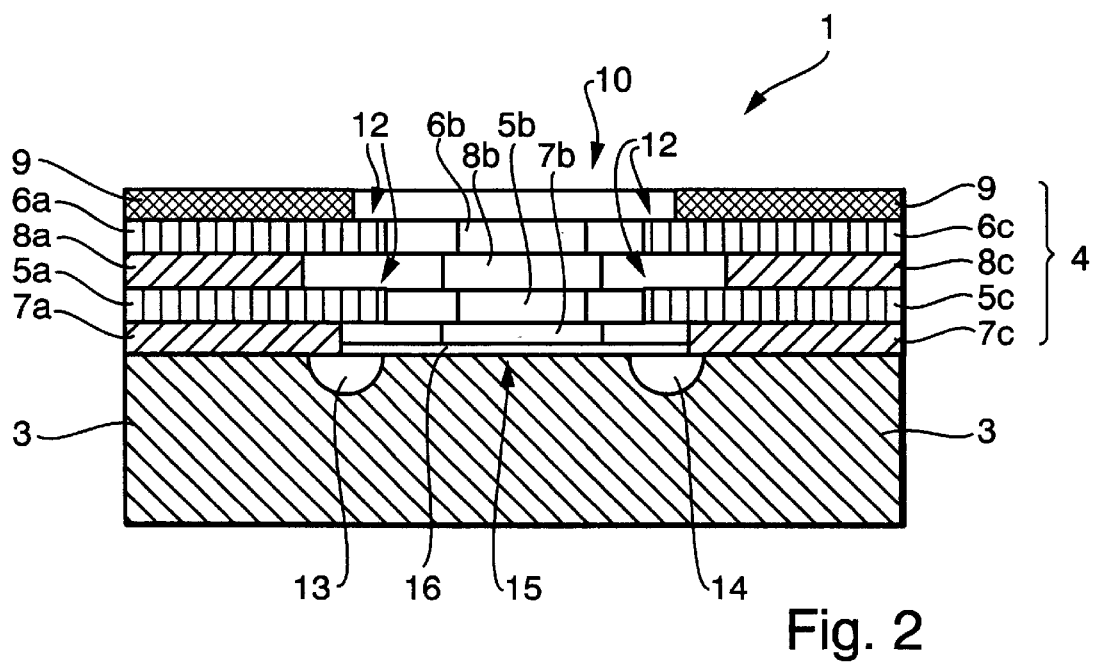
FIG. 2 is a representation similar to FIG. 1 where, however, the medium is not shown and where the layer stack has layers with several layer areas.

In FIGS. 1 and 2 it can be recognized that the side limiting walls of the recess 10 are profiled in layers. The electrically conductive layer areas 5a, 5b, 6a, 6b each form a projection 12 opposite the adjacent, electrically insulating layer areas 7a, 7b, 8a, 8b, 9a, 9b that are perpendicular to the coating planes of the layer stack 4. In this way, between each of the layer areas 5 a, 5b, 6a, 6b and the medium 2, an especially small electrical contact resistance is achieved. In FIGS. 1 and 2 it is recognizable that the limiting wall of the recess is set back, starting from the surface of the layer stack facing away from the substrate, down to the bottom of the recess at at least two positions, and that the limiting wall has at least one position projecting between these positions.

In the manufacture of the measuring device 1, the individual layers of the layer stack 4 are first mounted one after the other on the substrate layer 3, for example by vapor deposition, sputtering, galvanization or a similar known process for creating a layer. After completing the layer stack 4, an etch-proof mask is applied to the passivation layer 9a, 9b, which has an interruption or a recess in the region of the recess 10 to be made in-the layer stack 4. Then, the surface of the layer stack 4 having the mask and facing away from the substrate layer 3 is brought into contact with an etchant to make the recess 10. In order to make the profiling having the projections 12 and the indentations arranged respectively adjacent to it in the lateral limiting wall of the recess 10, the. individual layers of the layer stack 4 have different etching rates with regard to the etchant. In the embodiment according to FIG. 1, for example, the electrically insulating layers or layer areas 7a, 7b, 8a, 8b, 9a, 9b have a greater etching rate than the electrically conducting layers or layer areas 5a, 5b, 6a, 6b. In the area of the layers 7a, 7b, 8a, 8b an under-etching or an indentation results from this. Since the recess 10 is only etched into layer stack 4 after it is completed, the manufacturing process for the measuring device 1 can be integrated easily into the manufacturing process for semiconductor production.

Figure 3:
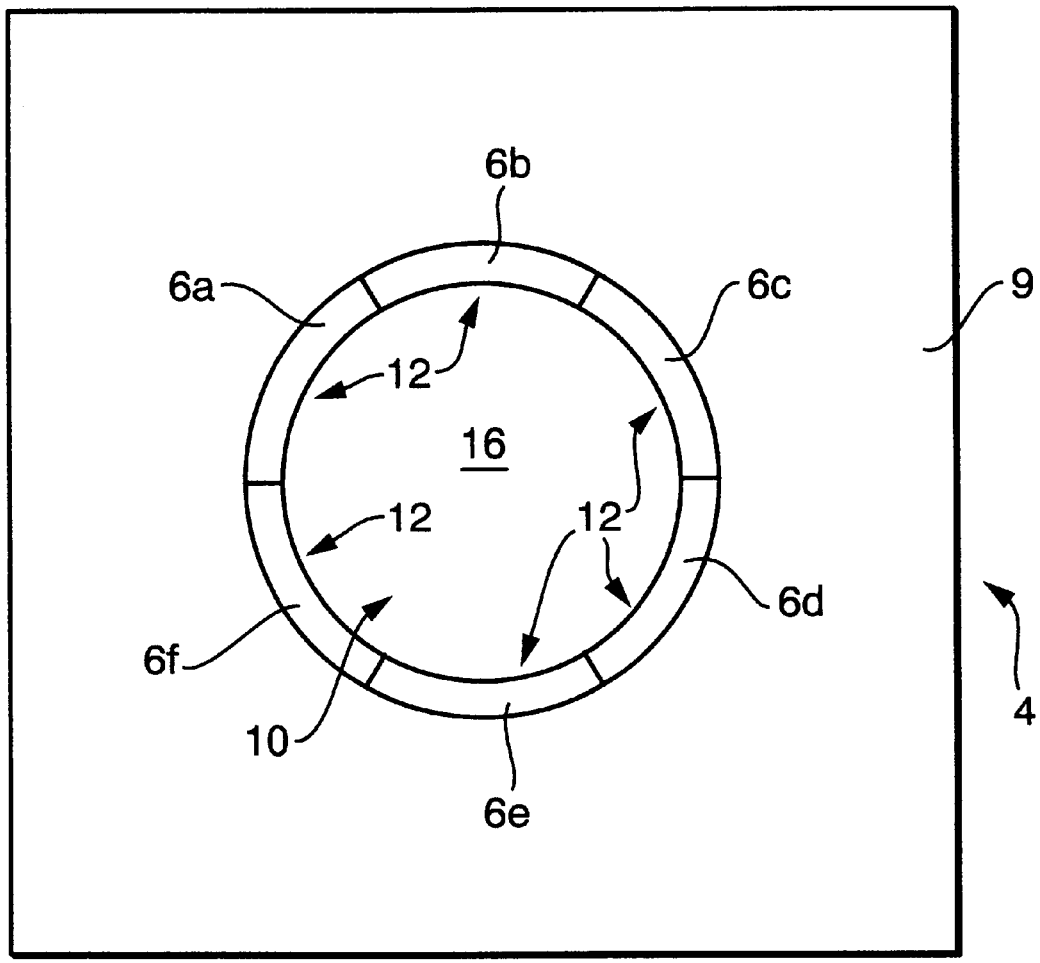
FIG. 3 is a view of the measurement device shown in FIG. 2.

In the embodiment according to FIG. 2, the recess 10 is constructed as a trough with a surrounding limiting wall (FIG. 3). The electrically conducting layers of the layer stack 4 each have several layer areas 5a, 5b, 5c, 6a, 6b, 6c, 6d, 6e, 6f that are electrically insulated from each other. Correspondingly, the optically conducting, electrically insulating layers of the layer stack 4 each have several layer areas 7a, 7b, 7c and 8a, 8b, 8c that are optically insulated from each other. The medium 2 can thus be electrically or optically examined or handled in this way in different directions in different coating planes of the layer stack 4. Thus, for example, between every two layer areas 6a, 6b, 6c, 6d, 6e, 6f that can be recognized in FIG. 3, electrical measurement lengths can be formed for directionally resolved measurement of the electrical conductivity of medium 2 in the coating plane of the layer.

In the embodiment according to FIGS. 1 and 2, a sensor is arranged on each bottom 11 of the recess 10, which sensor is constructed as an ion-selective field effect transistor with a drain area 13 and source area 14 integrated into the substrate layer 3. The electrically active gate area 15 of the sensor is arranged on the bottom of the recess 10 and galvanically separated from the medium 2 by an insulation layer 16. Using the sensor, additional examinations of the medium 2 are possible. Thus, for example,. electrical signals can be picked up using the sensor on particles contained in the medium 2, which can be biological cells or similar bio-components, for example.

It should also be mentioned that the layer stack can have a plurality of recesses 10, which can be arranged in the form of arrays, for example. Here, the electrically and/or optically conducting layer areas 5, 6, 7, 8 adjacent to the individual recesses 10 are preferably electrically and/or optically separated from each other, so that on the substrate layer 3 many measuring devices are produced, which are independent of each other, for examining the medium 2. The recesses 10 can have different dimensions for mechanically filtering particles contained in the medium 2.

In summary, a measuring device 1 is produced for examining a liquid or free-flowing medium 2, wherein the device has at least two electrically and/or optically conducting layers or layer areas 5a, 5b, 5c, 6a, 6b, 6c, 6d, 6e, 6f, which are located on a substrate layer 3 and are electrically and/or optically insulated from each other. At least one of these layers or layer areas 5a, 5b, 5c, 6a, 6b, 6c, 6d, 6e, 6f is a part of a layer stack 4, which has several layers arranged on top of each other on the substrate layer 3. On its side facing away from the substrate layer 3, the layer stack has a recess which adjoins the electrically and/or optically conducting layers or layer areas 5a, 5b, 5c, 6a, 6b, 6c, 6d, 6e, 6f. At least one electrically and/or optically conducting layer in the layer stack 4 or the at least one electrically and/or optically conducting layer area 5a, 5b, 5c, 6a, 6b, 6c, 6d, 6e, 6f in the layer stack is arranged at spaced from the bottom 11 of the recess 10.

It will be appreciated by those skilled in the art that changes could be made to the embodiment(s) described above without departing from the broad inventive concept thereof. It is understood, therefore, that this invention is not limited to the particular embodiment(s) disclosed, but it is intended to cover modifications within the spirit and scope of the present invention as defined by the appended claims.

We claim:

1. A measuring device for examining a medium, especially a liquid or free-flowing medium, comprising at least two electrically and/or optically conducting layers or layer areas made of a solid material and located on a substrate layer, the layers or layer areas being electrically and/or optically insulated from each other, at least one of the layers or layer areas being arranged in a layer stack having several layers arranged on top of each other on the substrate layer, the layer stack having, on its side facing away from the substrate layer, a recess that adjoins the electrically and/or optically conducting layers or layer areas, wherein at least one electrically and/or optically conducting layer or one layer area located in the layer stack is spaced at a distance from a bottom of the recess, wherein at least one layer of the layer stack has at least two electrically and/or optically conducting layer areas arranged next to each other in a coating plane of said at least one layer, which areas are each adjacent to the recess and are insulated from each other electrically and/or optically.

2. The measuring device according to claim 1, wherein the bottom of the recess is formed by at least one electrically and/or optically conducting layer or layer area.

3. The measuring device according to claim 1, wherein on a limiting wall of the recess at least one electrically and/or optically conducting layer area forms a projection opposite at least one layer area adjacent to it, and the layer area having the projection and the layer area adjacent to it are arranged in different coating planes of the layer stack.

4. A measuring device for examining a medium, especially a liquid or free-flowing medium, comprising at least two electrically and/or optically conducting layers or layer areas made of a solid material and located on a substrate layer, the layers or layer areas being electrically and/or optically insulated from each other, at least one of the layers or layer areas being arranged in a layer stack having several layers arranged on top of each other on the substrate layer, the layer stack having, on its side facing away from the substrate layer, a recess that adjoins the electrically and/or optically conducting layers or layer areas, wherein at least one electrically and/or optically conducting layer or one layer area located in the layer stack is spaced at a distance from a bottom of the recess, wherein a metallic layer or layer area is arranged as an optical reflection layer transverse to a coating plane on each side of an optically conducting layer or layer area.

5. A measuring device for examining a medium, especially a liquid or free-flowing medium, comprising at least two electrically and/or optically conducting layers or layer areas made of a solid material and located on a substrate layer, the layers or layer areas being electrically and/or optically insulated from each other, at least one of the layers or layer areas being arranged in a layer stack having several layers arranged on top of each other on the substrate layer, the layer stack having, on its side facing away from the substrate layer, a recess that adjoins the electrically and/or optically conducting layers or layer areas, wherein at least one electrically and/or optically conducting layer or one layer area located in the layer stack is spaced at a distance from a bottom of the recess, the measuring device including at least one optically conducting layer or layer area, wherein a limiting wall of the recess has at least one coupling location, located on the at least one optically conducting layer or layer area, for targeted emission of optical radiation into the recess, wherein at least one uncoupling position located on an optically transparent layer or layer area is arranged in the limiting wall lying opposite the coupling position in the emission direction of the radiation, and wherein the coupling position and/or the uncoupling position is (are) arranged on a projection projecting into the recess beyond the layers on both sides adjacent to it and can be extended against a restoring force of its material from a rest position transverse to a coating plane of the layer having the projection.

6. A measuring device for examining a medium, especially a liquid or free-flowing medium, comprising at least two electrically and/or optically conducting layers or layer areas made of a solid material and located on a substrate layer, the layers or layer areas being electrically and/or optically insulated from each other, at least one of the layers or layer areas being arranged in a layer stack having several layers arranged on top of each other on the substrate layer, the layer stack having, on its side facing away from the substrate layer, a recess that adjoins the electrically and/or optically conducting layers or layer areas, wherein at least one electrically and/or optically conducting layer or one layer area located in the layer stack is spaced at a distance from a bottom of the recess, wherein at least one sensor is arranged in the bottom of the recess for examining the medium located in the recess.

7. A measuring device for examining a medium, especially a liquid or free-flowing medium, comprising at least two electrically and/or optically conducting layers or layer areas made of a solid material and located on a substrate layer, the layers or layer areas being electrically and/or optically insulated from each other, at least one of the layers or layer areas being arranged in a layer stack having several layers arranged on top of each other on the substrate layer, the layer stack having, on its side facing away from the substrate layer, a recess that adjoins the electrically and/or optically conducting layers or layer areas, wherein at least one electrically and/or optically conducting layer or one layer area located in the layer stack is spaced at a distance from a bottom of the recess, wherein an ion-selective membrane is arranged in the recess and grasps behind a projection of a limiting wall of the recess.

8. A measuring device for examining a medium, especially a liquid or free-flowing medium, comprising at least two electrically and/or optically conducting layers or layer areas made of a solid material and located on a substrate layer, the layers or layer areas being electrically and/or optically insulated from each other, at least one of the layers or layer areas being arranged in a layer stack having several layers arranged on top of each other on the substrate layer, the layer stack having, on its side facing away from the substrate layer, a plurality of recesses having different dimensions and arranged in an array-shape, each recess adjoining at least two electrically and/or optically conducting layers or layer areas, and at least one electrically and/or optically conducting layer or layer area adjoining the respective recess being arranged at a distance from a bottom of the recess.

9. A process for manufacturing a measuring device for examining a medium, especially a liquid or free-flowing medium, comprising mounting at least two electrically and/or optically conducting layers or layer areas made of a solid material on a substrate layer, the layers or layer areas being electrically and/or optically insulated from each other and at least one of the layers or layer areas having several layers arranged on top of each other on the substrate layer to form a layer stack, arranging at least one electrically and/or optically insulating intermediate layer between the conducting layers, wherein the layer stack is provided by creating at least one electrically and/or optically insulating layer and at least one electrically and/or optically conducting layer, wherein the electrically and/or optically conducting layer is subdivided into at least two electrically and/or optically conducting layer areas which are electrically and/or optically insulated from each other, and forming a recess in the layer stack on a side of the layer stack facing away from the substrate layer such that the recess penetrates and/or adjoins the electrically and/or optically conducting layers or layer areas, wherein at least one electrically and/or optically conducting layer or one layer area located in the layer stack is spaced at a distance from a bottom of the recess.

10. The process for manufacturing a measuring device according to claim 9, wherein the layer stack is provided by mounting at least one electrically and/or optically insulating first layer and at least one electrically and/or optically conducting second layer on the substrate layer, wherein the recess is created in the layer stack on the side of the layer stack facing away from the substrate layer penetrating and/or adjoining the electrically and/or optically conducting second layer, and at least one electrically and/or optically conducting third layer is arranged on the bottom of the recess at a distance from the second layer.

11. The process according to claim 9, wherein an indentation relative to an adjacent electrically and/or optically conducting layer or layer area is formed by removing layer material on a limiting wall of the recess in a region of an electrically and/or optically insulating layer or layer area.

12. The process according to claim 11, wherein the layer stack is brought into contact with an etchant to create the recess, and layer materials of individual layers and/or layer areas are selected so as to have different etching rates with regard to the etchant in order to form an indentation in the limiting wall of the recess.

13. A process for manufacturing a measuring device for examining a medium, especially a liquid or free-flowing medium, comprising mounting at least two electrically and/or optically conducting layers or layer areas made of a solid material on a substrate layer, the layers or layer areas being electrically and/or optically insulated from each other and at least one of the layers or layer areas having several layers arranged on top of each other on the substrate layer to form a layer stack, arranging at least one electrically and/or optically insulating intermediate layer between the conducting layers, and forming a recess in the layer stack on a side of the layer stack facing away from the substrate layer such that the recess penetrates and/or adjoins the electrically and/or optically conducting layers or layer areas, wherein at least one electrically and/or optically conducting layer or one layer area located in the layer stack is spaced at a distance from a bottom of the recess, wherein the substrate is provided with a layer stack having a metallic layer or layer area as an optical reflection layer transverse to a coating plane of the layers of the layer stack on both sides of an optically conducting layer or layer area.

14. A process for manufacturing a measuring device for examining a medium, especially a liquid or free-flowing medium, comprising mounting at least two electrically and/or optically conducting layers or layer areas made of a solid material on a substrate layer, the layers or layer areas being electrically and/or optically insulated from each other and at least one of the layers or layer areas having several layers arranged on top of each other on the substrate layer to form a layer stack, arranging at least one electrically and/or optically insulating intermediate layer between the conducting layers, and forming a recess in the layer stack on a side of the layer stack facing away from the substrate layer such that the recess penetrates and/or adjoins the electrically and/or optically conducting layers or layer areas, wherein at least one electrically and/or optically conducting layer or one layer area located in the layer stack is spaced at a distance from a bottom of the recess, wherein a sensor is arranged in the bottom of the recess or in an area of the substrate provided for the bottom or for the layer stack.

15. A process for manufacturing a measuring device for examining a medium, especially a liquid or free-flowing medium, comprising mounting at least two electrically and/or optically conducting layers or layer areas made of a solid material on a substrate layer, the layers or layer areas being electrically and/or optically insulated from each other and at least one of the layers or layer areas having several layers arranged on top of each other on the substrate layer to form a layer stack, arranging at least one electrically and/or optically insulating intermediate layer between the conducting layers, and forming a recess in the layer stack on a side of the layer stack facing away from the substrate layer such that the recess penetrates and/or adjoins the electrically and/or optically conducting layers or layer areas, wherein at least one electrically and/or optically conducting layer or one layer area located in the layer stack is spaced at a distance from a bottom of the recess, wherein an ion-selective membrane is mounted in the recess.

16. A process for manufacturing a measuring device for examining a medium, especially a liquid or free-flowing medium, comprising mounting at least two electrically and/or optically conducting layers or layer areas made of a solid material on a substrate layer, the layers or layer areas being electrically and/or optically insulated from each other and at least one of the layers or layer areas having several layers arranged on top of each other on the substrate layer to form a layer stack, arranging at least one electrically and/or optically insulating intermediate layer between the conducting layers, and forming a recess in the layer stack on a side of the layer stack facing away from the substrate layer such that the recess penetrates and/or adjoins the electrically and/or optically conducting layers or layer areas, wherein at least one electrically and/or optically conducting layer or one layer area located in the layer stack is spaced at a distance from a bottom of the recess, wherein a plurality of recesses arranged in an array shape and having different dimensions are formed in the layer stack.

17. A measuring device for examining a medium, especially a liquid or free-flowing medium, comprising at least two electrically and/or optically conducting layers or layer areas made of a solid material and located on a substrate layer, the layers or layer areas being electrically and/or optically insulated from each other, at least one of the layers or layer areas being arranged in a layer stack having several layers arranged on top of each other on the substrate layer, the layer stack having, on its side facing away from the substrate layer, a recess that adjoins the electrically and/or optically conducting layers or layer areas, wherein at least one electrically and/or optically conducting layer or one layer area located in the layer stack is spaced at a distance from a bottom of the recess, wherein the at least one electrically and/or optically conducting layer forms a measuring element for electrically and/or optically examining a medium to be inserted into the recess.

* * * * *